United States Patent [19]

Emonds-Alt et al.

[11] Patent Number: 5,606,065

[45] Date of Patent: Feb. 25, 1997

[54] PROCESS FOR PREPARING N-ALKYLENE PIPERIDINO COMPOUNDS AND THEIR ENANTIOMERS

[75] Inventors: Xavier Emonds-Alt, Combaillaux; Serge Martinez, Montpellier; Vincenzo Proietto, Saint Georges d'Orques; Didier Van Broeck, Murviel les Montpellier, all of France

[73] Assignee: Sanofi, Paris, France

[21] Appl. No.: 410,292

[22] Filed: Mar. 24, 1995

Related U.S. Application Data

[62] Division of Ser. No. 877,734, May 4, 1992, Pat. No. 5,411,971.

[30] Foreign Application Priority Data

May 3, 1991 [FR] France .................................... 91 05486

[51] Int. Cl.⁶ ..................... C07D 413/12; C07D 401/12; C07D 211/58
[52] U.S. Cl. ................... 546/223; 546/205; 546/217; 546/224; 544/130
[58] Field of Search .......................... 544/130; 546/205, 546/217, 223, 224

[56] References Cited

U.S. PATENT DOCUMENTS

| | | | |
|---|---|---|---|
| 3,998,834 | 12/1976 | Janssen et al. | 260/293.68 |
| 4,134,982 | 1/1979 | Wise et al. | 424/263 |
| 4,179,569 | 12/1979 | Janssen et al. | 546/223 |
| 4,246,267 | 1/1981 | Vincent et al. | 424/267 |

*Primary Examiner*—Zinna Northington Davis
*Attorney, Agent, or Firm*—Foley & Lardner

[57] ABSTRACT

The invention relates to N-alkylenepiperidino compounds of formula

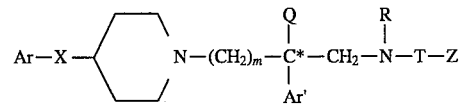

as well as their enantiomers, a process for preparing them and pharmaceutical compositions containing them.

These compounds are useful as antagonists of neurokinin receptors in the treatment of substance P- and/or neurokinin-dependent pathologies.

7 Claims, No Drawings

PROCESS FOR PREPARING N-ALKYLENE PIPERIDINO COMPOUNDS AND THEIR ENANTIOMERS

This application is a division, of application Ser. No. 07/877,734, filed May 4, 1992 now U.S. Pat. No. 5,411,971.

The present invention relates to new aromatic derivatives substituted with an amino group and with various amine or amide functions, and to their enantiomers.

The present invention also relates to the process for obtaining the compounds, which may be enantio-selective, and to the use of the compounds according to the invention in compositions for therapeutic application, and more especially in pathological phenomena involving the neurokinin system such as: pain (D. REGOLI et al., Life Sciences, 1987, 40, 109–117), allergy and inflammation (J. E. MORLAY et al., Life Sciences, 1987, 41, 527–544), circulatory insufficiency (J. LOSAY et al., 1977, Substance P, von Euler, U.S. and Pernow ed., 287–293, Raven Press, New York), gastrointestinal complaints (D. REGOLI et al., Trends Pharmacol. Sci., 1985, 6, 481–484), respiratory complaints (J. MIZRAHI et al., Pharmacology, 1982, 25, 39–50).

Endogenous ligands for neurokinin receptors have been described, such as substance P (SP), neurokinin A (NKA) (S. J. BAILEY et al., 1983, Substance P, P. Skrabanck ed., 16–17 Boole Press, Dublin) and neurokinin B (NKB) (S. P. WATSON, Life Sciences, 1983, 25, 797–808).

Neurokinin receptors have been recognised on numerous preparations, and are currently classified into three types: $NK_1$, $NK_2$ and $NK_3$. Whereas most preparations studied hitherto possess several types of receptors, such as guinea pig ileum ($NK_1$, $NK_2$ and $NK_3$), some of them appear to possess only one type, such as dog carotid artery ($NK_1$), rabbit pulmonary artery bereft of endothelium ($NK_2$) and rat portal vein ($NK_3$) (D. REGOLI et al., Trends Pharmacol. Sci., 1988, 9, 290–295 and Pharmacology, 1989, 38, 1–15).

A more precise characterisation of the different receptors is made possible by the recent synthesis of selective agonists. Thus, [$Sar^9$, $Met$-$(O_2)^{11}$]SP, [$Nle^{10}$]$NKA_{4-10}$ and [Me Phe$^7$]NKB appear to exhibit a respective selectivity for $NK_1$, $NK_2$ and $NK_3$ receptors (see D. REGOLI, 1988 and 1989 cited above).

It has now been found that some aromatic amino compounds possess advantageous pharmacological properties as neurokinin receptor antagonists, and are useful, in particular, for the treatment of any substance P- and neurokinin-dependent pathology.

Thus, according to one of its aspects, the present invention relates to aromatic amino derivatives of formula:

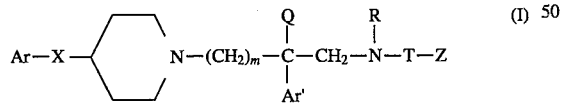

(I)

in which:

m is equal to 2 or 3;

Ar represents a phenyl, unsubstituted or substituted one or more times with a halogen atom, preferably a chlorine or fluorine atom, with a $C_1$–$C_3$ alkyl, with a trifluoromethyl, with an alkoxy in which the alkyl is a $C_1$–$C_3$ group, with a hydroxyl or with a methylenedioxy; a thienyl, pyridyl or imidazolyl group which is or is not substituted with a $C_1$–$C_3$ alkyl;

Ar' represents a phenyl group, unsubstituted or mono- or di-substituted with a halogen atom, preferably a chlorine or fluorine atom, with a $C_1$–$C_3$ alkyl, with a trifluoromethyl, with an alkoxy in which the alkyl is a $C_1$–$C_3$ group, with a hydroxyl or with a methylenedioxy; a thienyl group; an imidazolyl group or a benzothienyl group, each of which is unsubstituted or substituted with a halogen, preferably with a chlorine or fluorine atom; a naphthyl group unsubstituted or substituted with a halogen, preferably with a fluorine atom; a biphenyl group; an indolyl unsubstituted or substituted on the nitrogen with a benzyl group;

X represents an oxygen atom, a sulphur atom, a sulphone or a sulphoxide, an

group, an

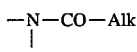

group or an

group in which Alk is a $C_1$–$C_3$ alkyl group; an

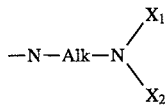

group in which Alk represents a $C_1$–$C_3$ alkylene and $X_1$ and $X_2$ represent, independently, hydrogen, a $C_1$–$C_3$ alkyl or form, together with the nitrogen atom to which they are bonded, a heterocycle chosen from amongst pyrrolidine, piperidine or morpholine;

Q represents hydrogen, a $C_1$–$C_4$ alkyl group or an aminoalkyl group of formula $-(CH_2)_q$–Am', where q is 2 or 3 and Am' is a piperidino, 4-benzylpiperidino or dialkylamino group, it being possible for each alkyl to contain 1 to 4 carbon atoms;

R represents hydrogen, a methyl group or a group $(CH_2)_n$—L, where n is an integer from 2 to 6 and L is hydrogen or an amino group;

T represents a group selected from

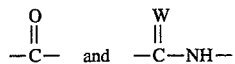

W being an oxygen or sulphur atom, and

Z represents either M or OM when T represents the

group, or M when T represents the group

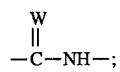

M represents hydrogen or a linear or branched $C_1$–$C_6$ alkyl; an α-hydroxybenzyl, an α-alkylbenzyl or a phenylalkyl in which the alkyl contains 1 to 3 carbon atoms, unsubstituted, mono- or polysubstituted on the aromatic ring with a halogen, a hydroxyl, an alkoxy of 1 to 4 carbon atoms, an alkyl of 1 to 4 carbon atoms; a pyridylalkyl in which the alkyl group contains 1 to 3 carbon atoms; a naphthylalkyl in which the alkyl group contains 1 to 3 carbon atoms; a pyridylthioalkyl in which the alkyl group contains 1 to 3 carbon atoms; a styryl; a 1-methyl-2-imidazolylthioalkyl in which the alkyl group contains 1 to 3 carbon atoms; a 1-oxophenyl-3-indan-2-yl; an unsubstituted, mono- or polysubstituted aromatic or heteroaromatic group;

or one of their salts with inorganic or organic acids or one of their quaternary ammonium salts. The quaternary ammonium salts of the compounds of formula (I) are formed from the piperidine nitrogen. The

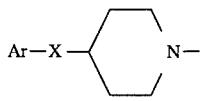

group is then represented by the group:

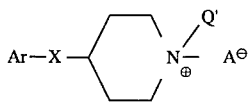

in which

Q' represents a $C_1$–$C_6$ alkyl group or a benzyl group and

A⊖ represents an anion chosen from amongst chloride, bromide, iodide, acetate, methanesulphonate or paratoluenesulphonate.

The salts of the compounds of formula (I) according to the present invention comprise both those with inorganic or organic acids which permit a suitable crystallisation or separation of the compounds of formula (I), such as picric acid or oxalic acid or an optically active acid, for example a mandelic or camphorsulphonic acid, and those which form pharmaceutically acceptable salts such as the hydrochloride, hydrobromide, sulphate, hydrogen sulphate, dihydrogen phosphate, methanesulphonate, methylsulphate, maleate, fumarate, 2-naphthalenesulphonate, glycolate, gluconate, citrate or isethionate.

In particular, in the formula (I), Z represents a mono-, di- or tricyclic aromatic or heteroaromatic group, capable of bearing one or more substituents, in which a carbon atom of the aromatic carbocycle or aromatic heterocycle is linked directly to the group T.

More especially, the radical Z can be a phenyl group, which can be unsubstituted or optionally contain one or more substituents.

When Z is a phenyl group, the latter can preferably be mono- or disubstituted, in particular 2,4-disubstituted, but also, for example, 2,3-, 4,5-, 3,4- or 3,5-disubstituted; it can also be trisubstituted, in particular 2,4,6-trisubstituted, but also, for example, 2,3,4-, 2,3,5-, 2,4,5- or 3,4,5-trisubstituted; tetra-substituted, for example 2,3,4,5-tetrasubstituted; or pentasubstituted. The substituents of the phenyl group can be: F;, Cl; Br; I, CN; OH; $NH_2$; NH—CO—$NH_2$; $NO_2$; $CONH_2$; $CF_3$; $C_1$–$C_{10}$ and preferably $C_1$–$C_4$ alkyl, methyl or ethyl being preferred, as well as, for example, n-propyl, isopropyl, n-butyl, isobutyl, sec-butyl, tert-butyl, pentyl or n-pentyl, hexyl or n-hexyl, heptyl or n-heptyl, octyl or n-octyl, nonyl or n-nonyl as well as decyl or n-decyl; alkenyl containing 2 to 10 and preferably 2–4 carbon atoms, for example vinyl, allyl, 1-propenyl, isopropenyl, butenyl or 1-buten-1-, -2-, -3- or -4-yl, 2-buten-1-yl, 2-buten-2-yl, pentenyl, hexenyl or decenyl; alkynyl containing 2 to 10 and preferably 2–4 carbon atoms, for example ethynyl, 1-pro-pyn-1-yl, propargyl, butynyl or 2-butyn-1-yl, pentynyl, decynyl; cycloalkyl containing 3 to 8 and preferably 5 or 6 carbon atoms, cyclopentyl or cyclohexyl being preferred, as well as, for example, cyclopropyl, cyclobutyl, 1-, 2- or 3-methylcyclopentyl, 1-, 2-, 3- or 4-methylcyclohexyl, cycloheptyl or cyclooctyl; bicycloalkyl containing 4 to 11 and preferably 7 carbon atoms, exo- or endo-2-norbornyl being preferred, as well as, for example, 2-isobornyl or 5-camphyl; hydroxyalkyl containing 1 to 5 and preferably 1–2 carbon atoms, hydroxymethyl and 1- or 2-hydroxyethyl being preferred, as well as, for example, 1-hydroxy-1-propyl, 2-hydroxy-1-propyl, 3-hydroxy-1-propyl, 1-hydroxy-2-propyl, 1-hydroxy-1-butyl, 1-hydroxy-1-pentyl; alkoxy containing 1 to 10 and preferably 1–4 carbon atoms, methoxy or ethoxy being preferred, as well as, for example, n-propoxy, isopropoxy, n-butoxy, isobutoxy, secbutoxy, tert-butoxy, pentyloxy, hexyloxy, heptyloxy, octyloxy, nonyloxy or decyloxy; alkoxyalkyl containing 2 to 10 and preferably from 2 to 6 carbon atoms, for example alkoxymethyl or alkoxyethyl such as methoxymethyl or 1- or 2-methoxyethyl, 1- or 2-n-butoxyethyl, 1- or 2-n-octyloxyethyl; alkoxyalkoxyalkyl containing from 3 to 10 and preferably from 4 to 7 carbon atoms, for example alkoxyalkoxymethyl, for example 2-methoxyethoxymethyl, 2-ethoxyethoxymethyl or 2-isopropoxyethoxymethyl, alkoxyalkoxyethyl, for example 2-(2-methoxyethoxy)ethyl or 2-(2-ethoxyethoxy)ethyl; alkoxyalkoxy containing from 2 to 10 and preferably from 3 to 6 carbon atoms, for example 2-methoxyethoxy, 2-ethoxyethoxy or 2-n-butoxyethoxy; alkenyloxy containing 2 to 10 and preferably 2 to 4 carbon atoms, allyloxy being preferred, as well as, for example, vinyloxy, propenyloxy, isopropenyloxy, butenyloxy such as 1-buten-1-, -2-, -3- or -4-yloxy, 2-buten-1-yloxy, 2-buten-2-yloxy, pentenyloxy, hexenyloxy or decenyloxy; alkenyloxyalkyl containing from 3 to 10 and preferably 3–6 carbon atoms, for example allyloxymethyl; alkynyloxy containing from 2 to 10 and preferably from 2 to 4 carbon atoms, propargyloxy being preferred, as well as, for example, ethynyloxy, 1-pro-pyn-1-yloxy, butynyloxy or 2-butyn-1-yloxy, pentynyloxy or decynyloxy; alkynyloxyalkyl containing from 3 to 10 and preferably 3 to 6 carbon atoms, for example ethynyloxymethyl, propargyloxymethyl or 2-(2-butyn-1-yloxy)ethyl; cycloalkoxy containing 3 to 8 and preferably 5 or 6 carbon atoms, cyclopentyloxy or cyclohexyloxy being preferred, as well as, for example, cyclopropyloxy, cyclobutyloxy, 1-, 2- or 3-methylcyclopentyloxy, 1-, 2-, 3- or 4-methylcyclohexyloxy, cycloheptyloxy or cyclooctyloxy; alkylthio containing from 1 to 10 and preferably 1 to 4 carbon atoms, methylthio or ethylthio being preferred, as well as, for example, n-propylthio, isopropylthio, n-butylthio, isobutylthio, sec-butylthio, tert-butylthio, pentylthio, hexylthio, octylthio, nonylthio or decylthio; alkylthioalkyl containing from 2 to 10 and preferably 2 to 6 carbon atoms, for example methylthiomethyl, 2-methylthioethyl or 2-n-butylthioethyl; acylamino, namely alkanoylamino containing from 1 to 7 and preferably 1 to 4 carbon atoms, formylamino and acetylamino being preferred, as well as propionylamino, butyrylamino, isobutyrylamino, valerylamino, caproylamino, heptanoylamino, as well as aroylamino or benzoylamino; acylaminoalkyl, preferably alkanoylaminoalkyl containing from 2 to 8 and preferably 3 to 6 carbon atoms, such as formylaminoethyl, acetylaminoethyl, propionylaminoethyl, n-butyrylaminoethyl, formylaminopropyl, acetylaminopropyl, propionylaminopropyl, formylaminobutyl, acetylaminobutyl, as well as propionylaminobutyl, butyrylaminobutyl; acyloxy containing from 1 to 6 and preferably 2 to 4 carbon atoms, acetyloxy, propionyloxy or butyryloxy being preferred, as well as, for example, formyloxy, valeryloxy, caproyloxy; alkoxycarbonyl containing from 2 to 5 and preferably 2 and 3 carbon atoms, methoxycarbonyl and ethoxycarbonyl being preferred, as well as, for example, n-propoxycarbonyl, isopropoxycarbonyl, n-butoxycarbonyl, isobutoxycarbonyl, sec-butoxycarbonyl or tert-butoxycarbonyl; cycloalkoxycarbonyl containing from 4 to 8 and preferably 6 or 7 carbon atoms, cyclopentyloxycarbonyl, cyclohexyloxycarbonyl being preferred, as well as cyclopropyloxycarbonyl, cyclobutyloxycarbonyl or cycloheptyloxycarbonyl; alkylaminocarbonylamino containing from 2 to 4 carbon atoms, such as methylaminocarbonylamino, ethylaminocarbonylamino, propylaminocarbonylamino; dialkylaminocarbonylamino containing from 3 to 7 and preferably 3 to 5 carbon atoms, preferably dimethylaminocarbonylamino, as well as di-n-propylaminocarbonylamino, diisopropylaminocarbonylamino; pyrrolidinocarbonylamino; piperidinocarbonylamino; cycloalkylaminocarbonylamino containing from 4 to 8 and preferably 6 or 7 carbon atoms, cyclopentylaminocarbonylamino, cyclohexylaminocarbonylamino being preferred, as well as cyclopropylaminocarbonylamino, cyclobutylaminocarbonylamino, cycloheptylaminocarbonylamino; alkylaminocarbonylaminoalkyl-containing from 3 to 9 and preferably 4 to 7 carbon atoms, methylaminocarbonylaminoethyl, ethylaminocarbonylaminoethyl, ethylaminocarbonylaminopropyl, ethylaminocarbonylaminobutyl being preferred, as well as, for example, methylaminocarbonylaminomethyl, n-propylaminocarbonylaminobutyl, n-butylaminocarbonylaminobutyl; dialkylaminocarbonylaminoalkyl containing from 4 to 11 carbon atoms, for example dimethylaminocarbonylaminomethyl, diethylaminocarbonylaminoethyl, diethylaminocarbonylaminopropyl, diethylaminocarbonylaminobutyl, pyrrolidinocarbonylaminoethyl, piperidinocarbonylaminoethyl; cycloalkylaminocarbonylaminoalkyl containing from 5 to 12 and preferably 8 to 11 carbon atoms, cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl and cyclohexylaminocarbonylaminobutyl being preferred, as well as, for example, cyclopropylaminocarbonylaminomethyl, cycloheptylaminocarbonylaminoethyl; alkoxycarbonylaminoalkyl containing from 3 to 12 and preferably 4 to 9 carbon atoms, methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, sec-butoxycarbonylaminoethyl, tertbutoxycarbonylaminoethyl, ethoxycarbonylaminopropyl, n-butoxycarbonylaminopropyl, ethoxycarbonylaminobutyl, n-butoxycarbonylaminobutyl being preferred, as well as, for example, n-propoxycarbonylaminopropyl, n-propoxycarbonylaminobutyl, isopropoxycarbonylaminobutyl; cycloalkoxycarbonylaminoalkyl containing from 5 to 12 and preferably 8 to 11 carbon atoms, cyclopentyloxycarbonylaminoethyl, cyclopentyloxycarbonylaminopropyl, cyclopentyloxycarbonylaminobutyl, cyclohexyloxycarbonylaminoethyl, cyclohexyloxycarbonylaminopropyl, cyclohexyloxycarbonylaminobutyl being preferred, as well as, for example, cyclopropyloxycarbonylaminomethyl, cycloheptyloxycarbonylaminoethyl; carbamoylalkyl containing from 2 to 5 and preferably 2 carbon atoms, preferably carbamoylmethyl, as well as carbamoylethyl, carbamoylpropyl, carbamoylbutyl; alkylaminocarbonylalkyl containing from 3 to 9 and preferably 2 to 6 carbon atoms, methylaminocarbonylethyl, ethylaminocarbonylmethyl, n-propylaminocarbonylmethyl, isopropylaminocarbonylmethyl, n-butylaminocarbonylmethyl, isobutylaminocarbonylmethyl, sec-butylaminocarbonylmethyl, tert-butylaminocarbonylmethyl being preferred, as well as, for example, ethylaminocarbonylethyl, ethylaminocarbonylpropyl, ethylaminocarbonylbutyl, n-propylaminocarbonylbutyl, n-butylaminocarbonylbutyl; dialkylaminocarbonylalkyl containing from 4 to 11 and preferably 4 to 8 carbon atoms, dimethylaminocarbonylmethyl, diethylaminocarbonylmethyl, di-n-propylaminocarbonylmethyl, as well as, for example, diethylaminocarbonylethyl, diethylaminocarbonylpropyl, diethylaminocarbonylbutyl; pyrrolidinocarbonylmethyl; piperidinocarbonylmethyl, piperidinocarbonylethyl; cycloalkylaminocarbonylalkyl containing from 5 to 12 and preferably 7 or 8 carbon atoms, cyclopentylaminocarbonylmethyl and cyclohexylaminocarbonylmethyl being preferred, as well as, for example, cyclopropylaminocarbonylmethyl, cyclobutylaminocarbonylmethyl, cycloheptylaminocarbonylmethyl, cyclohexylaminocarbonylethyl, cyclohexylaminocarbonylpropyl, cyclohexylaminocarbonylbutyl; alkylaminocarbonylalkoxy containing from 3 to 10 and preferably 3 to 5 carbon atoms, methylaminocarbonylmethoxy being preferred, as well as, for example, methylaminocarbonylethoxy, methylaminocarbonylpropoxy; dialkylaminocarbonylalkoxy containing from 4 to 10 and preferably 4 to 7 carbon atoms, such as dimethylaminocarbonylmethoxy, diethylaminocarbonylethoxy, (1-piperidyl)carbonylmethoxy; cycloalkylaminocarbonylalkoxy containing from 5 to 11 and preferably 7 or 8 carbon atoms, such as cyclopentylaminocarbonylmethoxy, cyclohexylaminocarbonylmethoxy.

The group Z is advantageously a phenyl group; a benzyl group; a benzoyl group; a phenylthioalkyl group in which the alkyl is a $C_1$–$C_3$ group.

The group Z is preferably mono- or disubstituted with a halogen or with $C_1$–$C_4$ alkoxy, the group 2,4-dichlorophenyl being particularly preferred.

The radical Z can also represent a bicyclic aromatic group such as 1- or 2-naphthyl; 1-, 2-, 3-, 4-, 5-, 6-, 7-indenyl; in which one or more bonds may be hydrogenated, it being possible for the said groups to be unsubstituted or optionally to contain one or more substituents such as: a halogen, and more particularly a fluorine atom, alkyl, phenyl, cyano, hydroxyalkyl, hydroxyl, oxo, alkylcarbonylamino, alkoxycarbonyl and thioalkyl groups, in which groups the alkyls are $C_1$–$C_4$ groups.

The radical Z can also be a pyridyl, thiadiazolyl, indolyl, indazolyl, imidazolyl, benzimidazolyl, benzotriazolyl, benzofuranyl, benzothienyl, benzothiazolyl, benzisothiazolyl, quinolyl, isoquinolyl, benzoxazolyl, benzisoxazolyl, benzoxazinyl, benzodioxinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl or chromanyl, in which one or more double bonds may be hydrogenated, it being possible for the said groups to be unsubstituted or optionally to contain one or more substituents such as alkyl, phenyl, cyano, hydroxyalkyl, hydroxyl, alkylcarbonylamino, alkoxycarbonyl and thioalkyl groups, in which groups the alkyls are $C_1$–$C_4$ groups.

The group Ar' is advantageously a phenyl and more particularly a phenyl substituted one or more times with a halogen, preferably with a chlorine atom.

According to another of its aspects, the present invention relates to a process for the preparation of differently substituted aromatic amino compounds of formula (I) and their salts, characterised in that a) a free amine of formula:

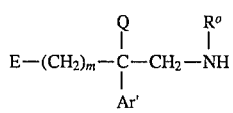
(II)

in which m, Ar' and Q are as defined above; R° represents hydrogen, a methyl group or a group $(CH_2)_n$—L° where n is as defined above and L° is hydrogen or an amino group protected by an N-protecting group; and E represents a hydroxyl group, an O-protected group such as tetrahydro-2-pyranyloxy, a mesyloxy group or a group

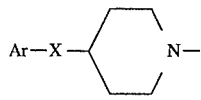

in which Ar and X are as defined above is treated
either with a functional derivative of an acid of formula:

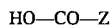
(III)

in which Z is as defined above, when a compound of formula (I) where T is —CO— is to be prepared,
or with an iso(thio)cyanate of formula:

(III')

in which W and Z are as defined above, when a compound of formula (I) where T is —C(W)—NH— is to be prepared, to form the compound of formula:

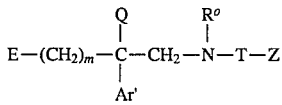
(IV)

b) then, when E represents tetrahydropyranyloxy, the tetrahydropyranyl group is removed by acid hydrolysis, it alternatively being possible for the hydrolysis to take place in step (a) on the starting amine of formula (II), c) the N-substituted alkanolamine thereby obtained, of formula:

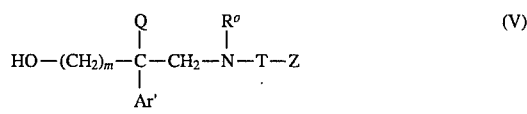
(V)

is treated with methanesulphonyl chloride, and d) the mesylate thereby obtained, of formula:

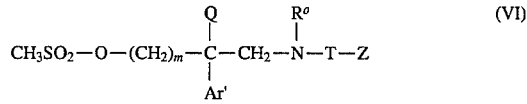
(VI)

is reacted with a secondary amine of formula:

(VII)

in which Ar and X are as defined above, e) the N-protecting groups, where appropriate, are removed and the product thereby obtained is optionally converted to one of its salts.

As a functional derivative of the acid (III), the acid itself is used, suitably activated, for example, with cyclohexylcarbodiimide or with benzotriazolyl-N-oxytris(dimethylamino)phosphonium hexafluorophosphate (BOP), or alternatively with one of the functional derivatives which react with amines, for example an anhydride, a mixed anhydride, the chloride or an activated ester, is used. When Z is a group OM, the acid in question is carbonic acid, and the monochloride, namely a chloroformate Cl—CO—OM, is used as a functional derivative.

The N-protecting groups optionally present in the group R° of the compound of the formula (II) are the conventional N-protecting groups well-known by the person skilled in the art and preferably those which can be removed by acid hydrolysis, such as the trityl, methoxytrityl or BOC group.

When a compound of formula (II) in which E represents a group

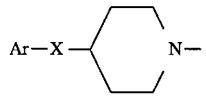

is used as starting material, the process of the present invention may be represented and illustrated in detail by Scheme 1 below:

SCHEME 1

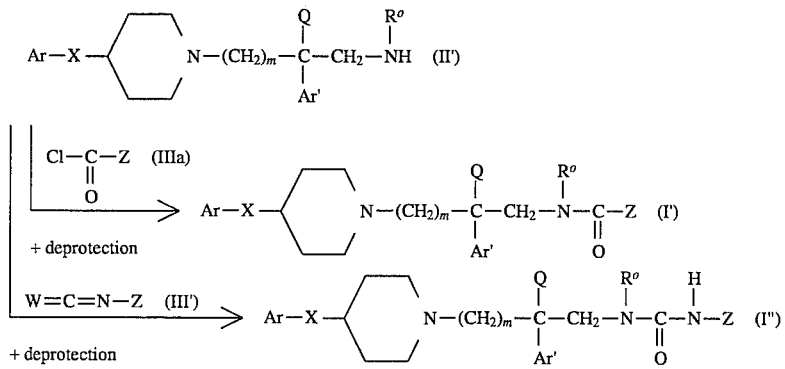

In the formula (IIIa) above, the acid chloride is considered to be the reactive functional derivative of the acid (III). The acid chloride is used when it is desired to prepare a compound (I') where Z is OM. The reaction with the acid chloride is performed in an inert solvent, such as dichloromethane or benzene in the presence of a base such as, for example, triethylamine at room temperature.

In the particular case of Z=OM, the reaction of the compound (II') with the chloroformate of the formula:

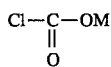

is performed by the usual methods.

When Z is other than OM, it is possible to use another functional derivative, or to start from the free acid (III), carrying out a coupling of (II') with BOP (benzotriazolyl-N-oxytris (dimethylamino) phosphonium hexafluorophosphate) and then adding the acid (III) in the presence of an organic base such as, for example, triethylamine, in a solvent such as dichloromethane or dimethylformamide, at room temperature, the compounds (I') obtained being isolated and purified according to the usual methods such as, for example, chromatography or recrystallisation.

It is also possible to react (II') with an iso(thio)cyanate W=C=N—Z (III') in an anhydrous inert solvent such as, for example, benzene, overnight at room temperature, and then to treat the reaction mixture according to the usual methods to obtain the compounds (I").

When a compound of formula (II) in which E represents a tetrahydropyranyloxy group is used as starting material, the process of the present invention may be represented and illustrated using Scheme 2.

The reactions of the compound (II") with the reagents (IIIa) and (III') proceed as described above for Scheme 1, it being possible for the acid chloride (IIIa) to be replaced by another functional derivative or by the free acid activated, for example, with BOP.

The intermediate (IV') thereby obtained is deprotected by acid hydrolysis to yield the free hydroxyl compound (V). The deprotection by hydrolysis of the tetrahydropyranyloxy group can be performed directly on the compound (II"). The hydroxylated compound (II''') is thereby obtained, which is reacted directly with the reagents (IIIa) or (III') as described in Scheme 2 below to give the compound (V). The mesylate (VI) is then prepared, the latter being substituted by a secondary amine of formula (VII) to obtain finally, after deprotection, where appropriate, of the amine L°, the compounds (I) according to the invention.

SCHEME 2

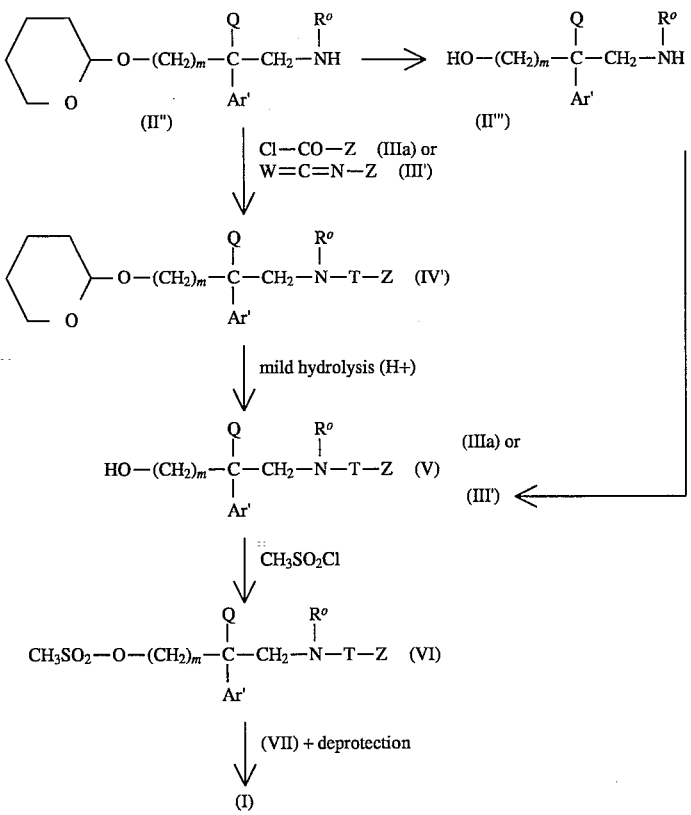

When the product obtained at the end of the reaction between the compound of formula (II) and the compound (III) (as the functional derivative) or (III'), has the formula IV where E represents a group

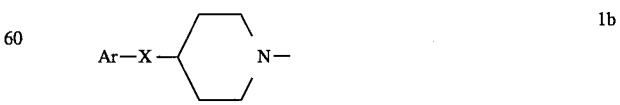

in which Ar and X are as defined above, the product can either represent the final product or have a protected amino group (L°). In the latter case, the N-protecting groups are hydrolysed according to the usual methods.

Deprotection is performed according to the known methods; particularly if, as O-protecting group, a tetrahydropyranyl group is used, the hydrolysis can be performed under mild conditions with dilute p-toluenesulphonic acid. If the molecule of the product (IV) at the same time contains a tetrahydropyranyloxy group and a tritylamino group, the hydrolysis of the first can therefore be performed while respecting the N-protecting group, even though formic acid liberates the two protecting groups at the same time.

The products of formula (I) thereby obtained are isolated, in the form of a free base or salt, according to conventional techniques.

When the compound of formula (I) is obtained in the form of a free base, salification is performed by treatment with the selected acid in an organic solvent. By treatment of the free base, dissolved, for example, in an alcohol such as isopropanol, with a solution of the selected acid in the same solvent, the corresponding salt is obtained, which salt is isolated according to conventional techniques. Thus, the hydrochloride, hydrobromide, sulphate, hydrogen sulphate, dihydrogen phosphate, methanesulphonate, oxalate, maleate, fumarate or 2-naphthalenesulphonate, for example, is prepared.

At the end of the reaction, the compounds of formula (I) may be isolated in the form of one of their salts, for example the hydrochloride or oxalate; in this case, if it is necessary, the free base may be prepared by neutralisation of the said salt with an inorganic or organic base such as sodium hydroxide or triethylamine, or with an alkali metal carbonate or bicarbonate such as sodium or potassium carbonate or bicarbonate.

The quaternary ammonium salts formed with the nitrogen of the piperidine are prepared by reaction of the free bases of the compounds (I), in which the other amino functions optionally present are N-protected by a customary N-protecting group, with an excess of alkylating agent of formula:

$$A—Q'$$

in which A represents a leaving group and is such as defined above for (I), preferably a chloride or an iodide, and Q' is such as defined above for (I), and the reaction mixture is heated in a solvent, for example chosen from amongst dichloromethane, chloroform, acetone or acetonitrile, at a temperature between room temperature and reflux for one to several hours to obtain, after treatment according to the customary methods and after deprotection if necessary, a mixture of axial and equatorial conformers of the quaternary ammonium salts.

Preferably, A⊖ represents an iodide which may be exchanged for another anion or for a pharmacologically acceptable anion, for example a chloride, by elution of the compound (I) on an ion exchange resin, for example Amberlite IRA68® or Duolite A375®.

The conformers are separated according to customary methods, for example by chromatography or by recrystallisation.

Each of the axial or equatorial conformers of the compounds (I) in racemic form or in the form of optically pure R or S enantiomers are part of the invention.

Resolution of the racemic mixtures (I) enables the enantiomers which form part of the invention to be isolated, It is also possible to perform the resolution of racemic mixtures of the products of formula (II), particularly of the products of formula (II') and (II'') or their precursors, in order to prepare the enantiomers of the products of formula (I). The resolution of the products of formula (II) is carried out according to EP-A-428434.

The starting compounds of formula (II) are prepared from nitriles of formula

in which m, E, Q and Ar' are as defined above, by reduction and, where appropriate, alkylation of the amine obtained.

For the preparation of the compounds of formula (II) where R° is hydrogen, the starting nitriles of formula (VIII) are subjected to a hydrogenation in an alkanol such as ethanol, in the presence of a catalyst such as, for example, Raney nickel, and the free primary amine may be isolated according to conventional methods.

When it is desired to prepare the compounds of formula (II) where R° is methyl, the free amine, obtained by hydrogenation of the nitrile (VIII) as described above, is treated with a chloroformate, for example with the chloroformate of formula Cl—CO—OAlk, where Alk is a $C_1$–$C_3$ alkyl, preferably ethyl, to obtain the carbamates of formula:

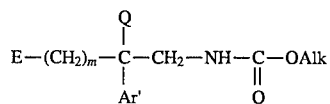

which are then reduced by known means such as the action of a reducing agent, for example a metal hydride such as sodium aluminium hydride or lithium aluminium hydride, or with a boron hydride such as borane dimethyl sulphide. The reduction is carried out in a solvent such as ether or toluene or at a temperature between room temperature and 60° C. The methylamine thereby obtained, of formula:

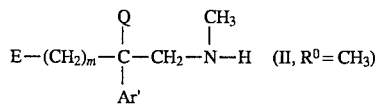

is isolated according to the usual methods.

To prepare the compounds of the formula (II) where R° is a group —$(CH_2)_n$—L°, where n and L° are as defined above, the free amine, obtained by hydrogenation of the nitrile (VIII) as described above, is treated with a reactive functional derivative of the acid of formula:

$$L°—(CH_2)_{n-1}—COOH \qquad (IX)$$

to obtain an amide of formula:

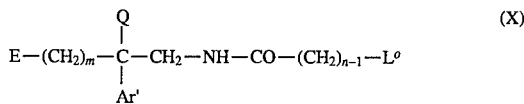

in which m, n, E, Ar', Q and L° are as defined above

The amide (X), by reduction under the same conditions as those described above for the nitrile (VIII), gives the desired compound of formula:

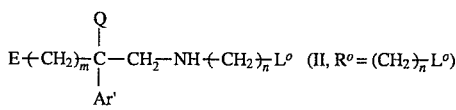

The nitriles of formula (VIII) are prepared from nitriles which are known, commercially available or prepared in accordance with known methods, of formula:

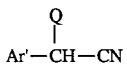 (XI)

which, by alkylation with a compound of formula $$E-(CH_2)_m-J \quad (XII)$$

in which m and E are as defined above and J is a halogen atom, for example a bromine atom, give the desired compounds (VIII).

Synthesis of the nitriles of formula (VIII) in which E is a tetrahydropyranyloxy group is preferably carried out from a tetrahydropyranyloxy (THP—O—) derivative obtained by reaction between an alkanol of formula Br—(CH$_2$)$_m$—OH, with m as defined above, and dihydropyran, to yield the compound

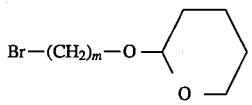

(XII, E = THP—O—, J = Br)

which is then reacted, in the presence of an alkali metal hydride, with the acetonitrile derivative (XI) to prepare the intermediate

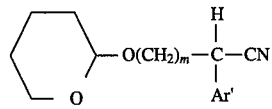

(VIII, E = THP—O—, Q = H)

corresponding to the compounds of formula (VIII) where Q is hydrogen; said compounds are precursors intermediate of compounds (If) described in scheme 1 above, it being possible for the intermediate prepared to be then alkylated.

Synthesis of the nitriles of formula (VIII) in which E represents a group

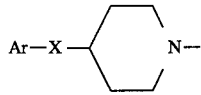

in which Ar and X are as defined above, is performed according to known methods by reaction with chlorinated derivatives of formula:

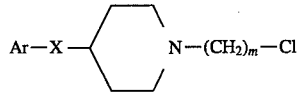 (XIII)

of a nitrile derivative of formula:

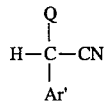 (XIV)

in the presence of sodium amide in a solvent such as toluene at temperatures of between 30° and 80° C.

The chlorinated derivative (XIII) is prepared by the action of a chlorinating reagent such as, for example, thionyl chloride on the hydroxyl derivative of formula:

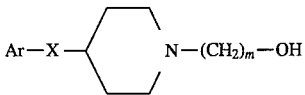 (XV)

which is itself prepared from the amine of formula:

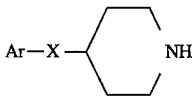 (VII')

which is reacted with ethylene oxide if m=2, and with a 3-halopropanol if m=3.

The starting amines of formula (II) in which the group E is a group of formula:

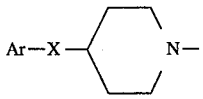

are novel compounds which are likewise part of the invention.

As indicated above, the intermediates which are capable of giving salts with optically active acids can be resolved in order to enable the preparation of the enantiomers of the compounds of formula (I).

It is equally possible to provide for the stereospecific synthesis of intermediates which do not give a salt enabling the separation.

An intermediate particularly adapted for such a stereospecific synthesis is the alcohol of formula (V) above.

Thus, according to another of its aspects, the present invention relates to the enantiomers and to a process for the preparation of the enantiomers of the compounds of formula I and of their salts; the said enantiomers correspond to the formula (I*) below:

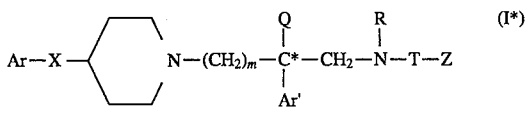 (I*)

in which:

Ar, Ar', Z, X, Q, R, T and m are as defined above and "*" signifies that the carbon atom thus marked has a determined (+) or (−) absolute configuration.

This process is characterised in that a compound of formula:

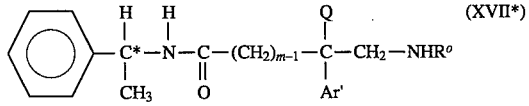 (XVII*)

is treated in a solvent such as, for example, dioxane, in acidic medium, for example in the presence of hydrochloric acid, to yield the amino acid of formula:

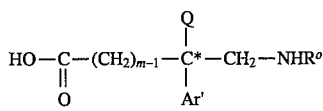 (XVIII*)

which is esterified in an alkanol AlkOH, where Alk is an alkyl of 1 to 4 carbon atoms, in acidic medium, then the corresponding ester of formula:

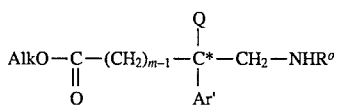 (XIX*)

in which Alk, Q, Ar', R° and m are as defined above, is treated either with a functional derivative of an acid of formula:

HO—CO—Z (III)

or with an iso(thio)cyanate of formula:

W=C=N—Z (III')

Z and W being as defined above, according to identical working conditions to those used for the preparation of the derivatives (IV) above, to obtain the ester of formula:

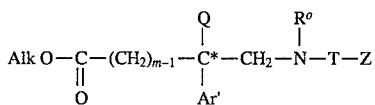 (XX*)

which is then reduced to the corresponding alcohol of formula:

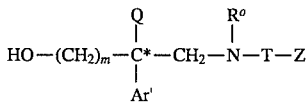 (V*)

The alcohol (V*) is converted to a methanesulphonate derivative of formula:

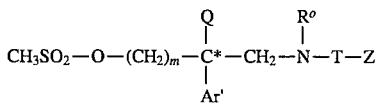 (VI*)

according to identical working conditions to those used for the preparation of the derivatives (VI) above.

The substitution of the mesylate (VI*) by a group of formula:

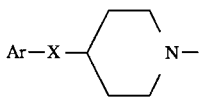 (VII)

according to the conditions described for obtaining (I) above enables the preparation of the derivatives (I*), after deprotection if appropriate, which are then optionally converted to one of their salts or to one of their quaternary ammonium salts according to the conventional methods of salification.

The compounds of the formula (XVII*) are known or can be easily prepared according to the method described by G. HELMCHEN et al., Angew. Chem. Int. Ed. Engl., 1979, 1, 18, 65;

according to the following scheme:

SCHEME 3

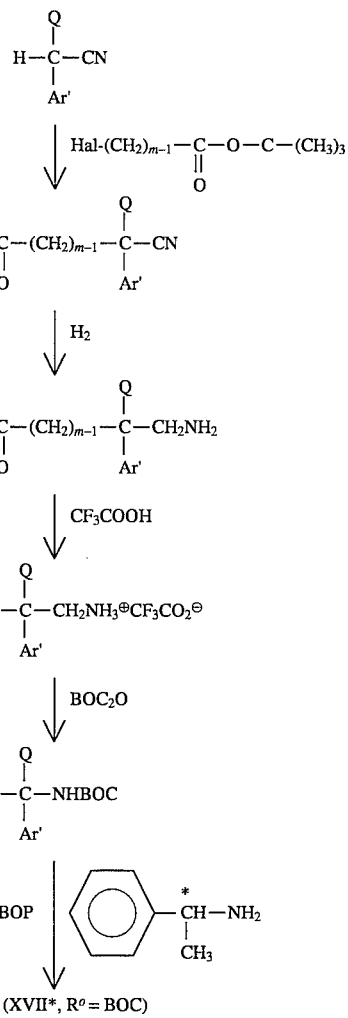

(XVII*, R° = BOC)

The products of formula (I*) thus obtained are isolated, in the form of free base or of a salt, according to the conventional techniques.

When the compound of formula (I*) is obtained in the form of free base, the salification is performed by treatment with the chosen acid in an organic solvent. By treatment of the free base, dissolved, for example, in an alcohol such as isopropanol, with a solution of the chosen acid in the same solvent, the corresponding salt is obtained, which is isolated according to the conventional techniques. Thus, for example, the hydrochloride, hydrobromide, sulphate, hydrogen sulphate, dihydrogen phospate, methanesulphonate, methylsulphate, oxalate, maleate, fumarate or 2-naphthalenesulphonate are prepared.

At the end of the reaction, the compounds of formula (I*) can be isolated in the form of one of their salts, for example the hydrochloride or the oxalate, or in the form of one of their quaternary ammonium salts; in this case, if it is necessary the free base can be prepared by neutralisation of the said salt with an inorganic or organic base.

The compounds according to the invention were subjected to biochemical tests.

The compounds (I) and (I*) and their salts showed antagonist properties with respect to binding to substance P in tests carried out on rat cortex membranes and IM9 lymphoblastic cells, according to M. A. CASCIERI et al., J. Biol. Chem., 1983, 258, 5158–5164 and D. D. PAYA et al., J. Immunol., 1984, 133, 3260–3265.

The same compounds and their salts showed antagonist properties with respect to binding to NKA in tests carried out on rat duodenum membranes according to L. BERGSTROM et al., Mol. Pharmacol., 1987, 32, 764–771.

The same compounds and their salts showed antagonist properties with respect to binding to eledoisin according to tests carried out on rat membranes according to A. C. Foster et al., Br. J. Pharmacol., 1988, 94, 602–608.

Eledoisin is a peptide of batrachian origin which is equivalent to neurokinin B.

The compounds according to the invention are antagonists of substance P, neurokinin A or neurokinin B.

Thus, compound 4 antagonises the binding substance P with a Ki of 41 nanomolar, compound 8 antagonises the binding of neurokinin A with a Ki of 5.5 nanomolar and compound 9 antagonises the binding of eledoisin with a Ki of 400 nanomolar.

The compounds of the present invention are generally administered in the form of dosage units. The said dosage units are preferably formulated in pharmaceutical compositions in which the active principle is mixed with a pharmaceutical excipient.

Thus, according to another of its aspects, the present invention relates to pharmaceutical compositions containing as active principle a compound of formula (I) or (I*) or one of their pharmaceutically acceptable salts.

The compounds of formula (I) or (I*) above and their pharmaceutically acceptable salts can be used in daily doses of 0.01 to 100 mg per kilo of body weight of the mammal to be treated, preferably in daily doses of 0.1 to 50 mg/kg. In a human, the dose may vary preferably from 0.5 to 4000 mg per day, more particularly from 2.5 to 1000 mg, according to the age of the subject to be treated or the type of treatment: prophylactic or curative.

In the pharmaceutical compositions of the present invention for oral, sublingual, subcutaneous, intramuscular, intravenous, transdermal, topical or rectal administration, the active principles may be administered in single-dose administration forms, mixed with conventional pharmaceutical carriers, to animals and to human beings. Suitable single-dose administration forms comprise oral forms such as tablets, gelatin capsules, powders, granules and solutions or suspensions to be taken by mouth, forms for sublingual and buccal administration, forms for subcutaneous, intramuscular, intravenous, intranasal or intraocular administration and forms for rectal administration.

When a solid composition is prepared in the form of tablets, the principal active principle is mixed with a pharmaceutical vehicle such as gelatin, starch, lactose, magnesium stearate, talc, gum arabic or the like. The tablets may be coated with sucrose or other suitable substances, or alternatively treated in such a way that they have sustained or delayed activity and continuously release a predetermined quantity of active principle, A preparation in the form of gelatin capsules is obtained by mixing the active principle with a diluent and pouring the mixture obtained into soft or hard gelatin capsules.

A preparation in the form of a syrup or elixir can contain the active principle together with a sweetener, preferably having zero energy content, and methylparaben and propylparaben as antiseptic, as well as an agent imparting flavour and a suitable colouring.

The water-dispersible powders or granules can contain the active principle mixed with dispersing agents or wetting agents or suspending agents such as polyvinylpyrrolidone, as well as with sweeteners or flavour correctors.

For rectal administration, suppositories which are prepared with binders melting at rectal temperature, for example cocoa butter or polyethylene glycols, are employed.

For parenteral, intranasal or intraocular administration, aqueous suspensions, isotonic saline solutions or sterile and injectable solutions which contain pharmacologically compatible dispersing agents and/or wetting agents, for example propylene glycol or butylene glycol, are used.

For administration by inhalation, an aerosol containing, for example, sorbitan trioleate or oleic acid, as well as trichlorofluoromethane, dichlorodifluoromethane, dichlorotetrafluoroethane or any other biologically compatible propellant gas, is used.

The active principle may also be formulated in the form of microcapsules, where appropriate with one or more carriers or additives.

The abovementioned compositions may also contain other active products such as, for example, bronchodilators, antitussives or antihistamines.

The examples which follow illustrate the invention without, however, limiting it.

The melting or decomposition points of the products, m.p., were measured on a Koffler heating block. The $^{13}C$ nuclear magnetic resonance spectra were performed at 50 MHz in dimethyl sulphoxide.

EXAMPLE 1

N-[4-(4-Phenoxy-1-piperidinyl)-2-(3,4-dichlorophenyl) butyl]-2,4-dichlorobenzamide hydrochloride

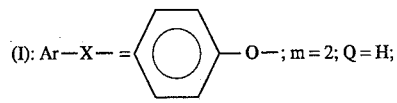

(I): Ar—X— = ; m = 2; Q = H;

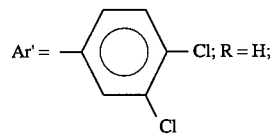

Ar' = ; Cl; R = H;

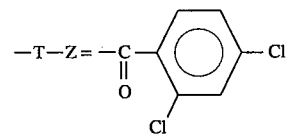

—T—Z= —C— ; Cl

A) Preparation of the amine:

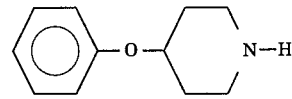

60.6 g of 4-hydroxypiperidine are dissolved in a mixture of 320 ml of dioxane and 80 ml of water. 144 g of BOC$_2$O are then added rapidly and the reaction mixture is heated at 80° C. for one and a half hours after the addition. It is concentrated in vacuo, the residue is taken up in ether and washed three times with water, and the ethereal phase is separated after settling has taken place, dried over Na$_2$SO$_4$, filtered and concentrated in vacuo to obtain 116 g of a yellowish oil which is dissolved in 300 ml of hexane and then crystallised to yield 100 g of crystals.

M.p.=68°–70° C.

100 g of the crystals prepared above and 55.5 g of triethylamine are dissolved in 500 ml of dichloromethane. 60.1 g of mesyl chloride are then added dropwise while cooling in ice. At the end of the addition, the reaction mixture is allowed to return to room temperature and left overnight. The dichloromethane is concentrated in vacuo and the residue is taken up in water and extracted with ethyl acetate. The organic phases are washed with water, then with a 5% solution of NaHCO$_3$ and then with a saturated solution of NaCl, and then concentrated in vacuo to yield crystals which are recrystallised in 250 ml of ethyl acetate to which 500 ml of hexane are added.

m=135.2 g

M.p.=99° C.

0.83 g of 55% sodium hydride in oil are suspended in 150 ml of dimethylformamide, then 3.67 g of phenol dissolved in 10 ml of dimethylformamide are added rapidly. The mixture is stirred at room temperature for 30 minutes then 8.37 g of the product obtained above are added and the reaction mixture is heated at 80° C. for 4 hours. The solvent is concentrated in vacuo, the residue is taken up in a solution of 10% sodium hydroxide and the mixture is extracted with ether. The ethereal phase is washed successively with a solution of 5% sodium hydroxide and then with a saturated solution of NaCl, dried over Na$_2$SO$_4$ and concentrated in vacuo. The residue obtained is treated with a solution of 30 ml of methanol heated to 50°–60° C., 10 ml of concentrated hydrochloric acid and 10 ml of water for one hour, and then the mixture is concentrated in vacuo and the residue is recrystallised in 100 ml of ethyl acetate.

m=3.44 g

B) Preparation of 1-(2,4-dichlorobenzoylamino)-2-(3,4-dichlorophenyl)-4-mesyloxybutane.

a) 3-(3,4-Dichlorophenyl)-1-(2-tetrahydropyranyloxy)-3-cyanopropane.

20 g of 55–60% sodium hydride in oil are suspended in 200 ml of dry tetrahydrofuran. A solution of 85 g of 3,4-dichlorophenylacetonitrile in 500 ml of tetrahydrofuran is added dropwise at 20° C., in the course of 30 minutes, then the reaction mixture is stirred at room temperature for 2 hours. The mixture is cooled to –20° C. and a solution of 98 g of 1-bromo-2-tetrahydropyranyloxyethane in 100 ml of tetrahydrofuran is added, the mixture is allowed to return to room temperature and after 2 hours a solution of 50 g of ammonium chloride in 3 liters of water is added. The mixture is extracted with 1.5 liters of ether, and the extract is washed with a saturated solution of sodium chloride, separated after settling has taken place, dried over MgSO$_4$ and concentrated in vacuo.

The residue is chromatographed on silica gel, eluent: dichloromethane. The fractions of pure product are concentrated in vacuo to yield 83.6 g of an oil.

b) 1-Amino-2-(3,4-dichlorophenyl)-4-(2-tetrahydropyranyloxy)butane.

83.6 g of the nitrile obtained above are dissolved in 100 ml of absolute ethanol. 350 mg of concentrated ammonia are added then, while flushing with nitrogen, Raney nickel is added (10% of the starting quantity of amine). The mixture is then hydrogenated under a hydrogen atmosphere at room temperature and atmospheric pressure.

11.9 liters of hydrogen are absorbed in 3 hours. The catalyst is separated by filtration on Celite, the filtrate is concentrated in vacuo, and the residue is taken up in a saturated solution of sodium chloride. After extracting with ether and drying over MgSO$_4$, 82.5 g of an oil are obtained.

c) 1-(2,4-Dichlorobenzoylamino)-2-(3,4-dichlorophenyl)-4-(2-tetrahydropyranyloxy)butane.

80 g of the amine obtained above are dissolved in 800 ml of dichloromethane. The solution is cooled to 0° C. and 38.4 ml of triethylamine and then 55 g of 2,4-dichlorobenzoyl chloride are added. The reaction mixture is then stirred at room temperature for one hour and thereafter washed with water. The organic phase is separated after settling has taken place, dried over MgSO$_4$ and concentrated in vacuo to yield 120 g of an oil.

d) 1-(2,4-Dichlorobenzoylamino)-2-(3,4-dichlorophenyl)butan-4-ol.

120 g of the product obtained above are dissolved in 1 liter of methanol in the presence of 12 g of paratoluenesulphonic acid. The reaction mixture is stirred for 18 hours at room temperature and then concentrated in vacuo. The residue is taken up in dichloromethane and washed with a 10% sodium carbonate solution. The organic phase is separated after settling has taken place and dried over MgSO$_4$ to yield 106 g of an oil.

e) 1-(2,4-Dichlorobenzoylamino)-2-(3,4-dichlorophenyl)-4-mesyloxybutane.

106 g of the alcohol obtained above are dissolved in 2 l of dichloromethane, and 44 ml of triethylamine and 24.2 ml of mesyl chloride are then added to the solution cooled to 0° C. The reaction mixture is stirred at 0° C. for 45 minutes, washed three times with ice-cold water, separated after settling has taken place, dried over MgSO$_4$ and concentrated in vacuo.

The residue is recrystallised from isopropyl ether.

m=95 g.

C) Compound 1.

A solution of 3.6 ml of triethylamine in 2 ml of dimethylformamide is prepared and 2.1 g of 4-phenoxypiperidine prepared above according to A and liberated with sodium hydroxide are then added slowly. 2.2 g of the methanesulphonate prepared according to B, step e, are then added to this solution, the reaction mixture is heated at 60° C. for one hour, 0.1 g of 4-phenoxypiperidine is added and the reaction mixture is heated again at 60° C. for 30 minutes. It is poured into water, extracted several times with ether, and the ethereal phases are separated after settling has taken place, dried over Na$_2$SO$_4$, filtered and concentrated in vacuo. The residue is chromatographed on silica gel, eluent: dichloromethane/methanol 93:3 (v/v) then 95:5 (v/v). Concentration of the pure fractions yields 1.9 g of the expected product in the form of base; the hydrochloride is then prepared in ethyl acetate.

m=1.5 g

M.p.=210° C.

EXAMPLE 2

N-[4-(4-Phenylthiopiperidinyl)-2-(3,4-dichlorophenyl)butyl]-4-fluoro-1-naphthalenecarboxamide hydrochloride

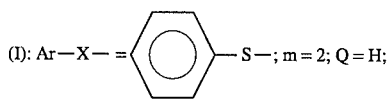

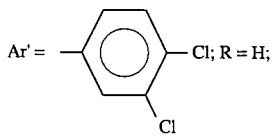

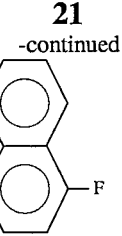

A) Preparation of the amine:

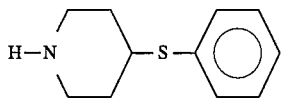

20.2 g of 4-hydroxypiperidine are dissolved in 80 ml of dioxane and 20 ml of water. 48 g of BOC$_2$O are added rapidly and the reaction mixture is heated under reflux overnight. The solvents are concentrated in vacuo and the residue is recrystallised in hexane.

30 g of crystals are obtained.

9.0 g of the product prepared above and 5 g of triethylamine are dissolved in 60 ml of dichloromethane and then a solution of 5.4 g of mesyl chloride in 20 ml of dichloromethane is added dropwise. The reaction mixture is stirred for two hours at room temperature and the solvents are concentrated in vacuo. The residue is taken up in water and extracted with ethyl acetate. The organic phases are separated and washed successively with a 5% NaHCO$_3$ solution and then with a saturated NaCl solution, dried over Na$_2$SO$_4$ and concentrated in vacuo. The residue is recrystallised in a mixture of ethyl acetate/hexane.

10.4 g of crystals are obtained.

1.5 g of 55% sodium hydride in oil are suspended in 150 ml of dimethylformamide and 4.29 g of thiophenol are then added at room temperature. After stirring for 30 minutes, 8.37 g of the product prepared above are added and the reaction mixture is left overnight at room temperature. The solvent is concentrated in vacuo, the residue is taken up in a sodium hydroxide solution and the mixture is extracted with ether. The organic phase is separated and washed successively with a 5% sodium hydroxide solution, once with water and then with a saturated NaCl solution, dried over Na$_2$SO$_4$ and concentrated in vacuo.

8.56 g of an oily residue are obtained.

8.5 g of the product obtained above are heated at 40°–50° C. in a mixture of 50 ml of methanol, 20 ml of concentrated hydrochloric acid and 10 ml of water for one and a half hours. The solvents are concentrated in vacuo and the residue is recrystallised in ethyl acetate.

m=5.42 g

M.p.=159°–161° C.

B) Preparation of 1-(4-fluoro-1-naphthoylamino)-2-(3,4-Dichlorophenyl)-4-mesyloxybutane.

a) 3-(3,4-Dichlorophenyl)-1-(2-tetrahydropyranyloxy)-3-cyanopropane.

20 g of 55–60% sodium hydride in oil are suspended in 200 ml of dry tetrahydrofuran. A solution of 85 g of 3,4-dichlorophenylacetonitrile in 500 ml of tetrahydrofuran is added dropwise at 20° C., in the course of 30 minutes and the reaction mixture is then stirred room temperature for 2 hours. The mixture is cooled to −20° C. and a solution of 98 g of 1-bromo-2-tetrahydropyranyloxyethane in 100 ml of tetrahydrofuran is added, the mixture is allowed to return to room temperature and, after two hours, a solution of 50 g of ammonium chloride in 3 liters of water is added. The mixture is extracted with 1.5 liters of ether, washed with a saturated sodium chloride solution, separated after settling has taken place, dried over MgSO$_4$ and concentrated in vacuo.

The residue is chromatographed on silica gel, eluent: dichloromethane. The fractions of pure product are concentrated in vacuo to yield 83.6 g of an oil.

b) 1-Amino-2-(3,4-dichlorophenyl)-4-(2-tetrahydropyranyloxy)butane.

83.6 g of the nitrile obtained above are dissolved in 100 ml of absolute ethanol. 350 ml of concentrated ammonia are added and then, while flushing with nitrogen, Raney nickel is added (10% of the quantity of starting amine). The mixture is then hydrogenated under a hydrogen atmosphere at room temperature and atmospheric pressure.

11.9 liters of hydrogen are absorbed in 3 hours. The catalyst is separated by filtration on Celite, the filtrate is concentrated in vacuo, and the residue is taken up in a saturated sodium chloride solution. After extracting with ether and drying over MgSO$_4$, 82.5 g of an oil are obtained.

c) 2-(3,4-Dichlorophenyl)-1-(4-fluoro-1-naphthoylamino)-4-(2-tetrahydropyranyloxy)butane.

4.8 g of amine prepared above and 3 ml of triethylamine are dissolved in 50 ml of methylene chloride. A solution of 5 g of 4-fluoronaphthoyl chloride in 10 ml of dichloromethane is then added dropwise. After the addition, the reaction mixture is heated under reflux for 15 minutes and concentrated in vacuo. The residue is taken up in water and extracted with ether. The ethereal phase is separated and washed successively with a 5% NaHCO$_3$ solution and a saturated NaCl solution. After drying over Na$_2$SO$_4$ and evaporating the solvents in vacuo, 7.35 g of an oil product are obtained.

d) 2-(3,4-Dichlorophenyl)-1-(4-fluoro-1-naphthoylamino)butan-4-ol.

4 ml of Amberlyst A® acid resin are added to a solution of 13 g of the compound obtained according to the preceding step c), in 80 ml of methanol, and the mixture is stirred for one hour at room temperature and heated under reflux for 30 minutes. The resin is separated by filtration on Celite and the filtrate is concentrated in vacuo.

m=10.7g.

e) 2-(3,4-Dichlorophenyl)-1-(4-fluoro-1-naphthoylamino)-4-mesyloxybutane.

4.3 g of triethylamine and then 3.5 g of mesyl chloride are added to a solution of 10.5 g of the alcohol obtained above in 100 ml of dichloromethane. At the end of the addition, the mixture is washed successively with water and then with a saturated NaCl solution. The organic phase is separated after settling has taken place, dried over Na$_2$SO$_4$ and concentrated in vacuo. The oil obtained crystallises in ether.

m=10.15 g

C) Compound 2.

2.3 g of the amine 4-phenylthiopiperidine prepared above (according to A) and liberated with sodium hydroxide, and 1.4 ml of triethylamine are dissolved in 10 ml of dimethylformamide, 2.8 g of mesylate prepared above are then added and the mixture is heated at 80° C. for 45 minutes. The mixture is poured into water and extracted with ethyl acetate. The organic phase is dried over Na$_2$SO$_4$ and concentrated in vacuo. The residue is chromatographed on silica gel, eluent: dichloromethane/methanol 93:7 (v/v) then 92:8 (v/v). Concentration of the pure fractions yields an oil which is dissolved in ethyl acetate. The addition of ethereal hydrogen chloride allows the hydrochloride to be prepared, which crystallises.

m=1 g

M.p.=211° C.

The compounds assembled in Table 1 are prepared by the procedures according to Examples 1 or 2 above.

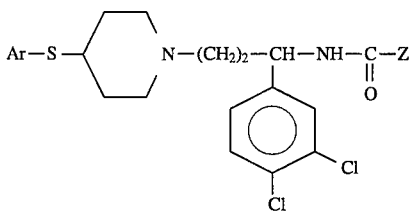

TABLE 1

| Example n° | Ar | Z | F;°C. | Salt |
|---|---|---|---|---|
| 3 | phenyl | 2,4-dichlorophenyl | 112 | HCl |
| 4 | pyridinyl | 2,4-dichlorophenyl | 178 | 2HCl |
| 5 | pyridinyl | 2,4-dichlorophenyl | 220 | 2HCl |
| 6 | pyridinyl | 8-fluoronaphthyl | 198 | 2HCl |

EXAMPLE 7

N-[4-(4-Anilino-1-piperidinyl)-2-(3,4-dichlorophenyl)butyl]-2,4-dichlorobenzamide dihydrochloride

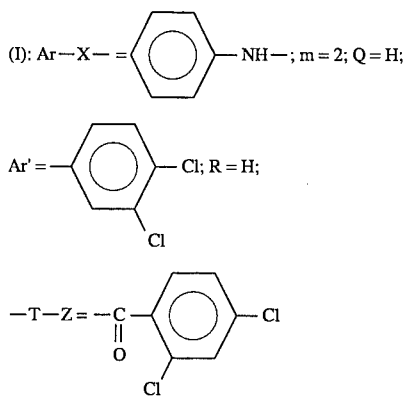

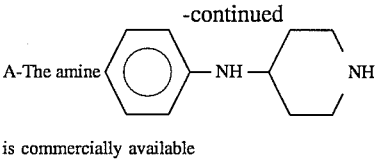

is commercially available

B) Compound 7

1 g of 1-(2,4-dichlorobenzoylamino)-2-(3,4-dichlorophenyl)-4-mesyloxybutane prepared as above in Example 1B and 0.8 g of 4-anilinopiperidine (commercially available) are dissolved in 1 ml of dimethylformamide and the reaction mixture is heated at 60° C. for one hour. The solution is then poured into water, the mixture is extracted with ethyl acetate, and the organic phase is separated and washed with water, dried over $Na_2SO_4$ and concentrated in vacuo. The residue is purified by silica gel chromatography, eluent: dichloromethane/methanol 97:3 (v/v).

Concentration of the pure fractions yields a residue which is converted into the hydrochloride and recrystallised in ethanol.

m=0.25 g
M.p.=214° C.

EXAMPLE 8

N-[4-(N'-4-Acetylanilino-1-piperidinyl)-2-(3,4-dichlorophenyl)butyl]-N-methylbenzamide hydrochloride

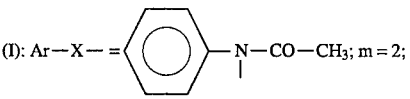

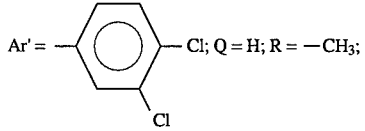

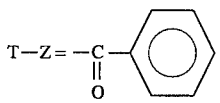

A) (3-(3,4-Dichlorophenyl)-1-(2-tetrahydropyranyloxy)-3-cyanopropane.

20 g of 55–60% sodium hydride in oil are suspended in 200 ml of dry tetrahydrofuran. A solution of 85 g of 3,4-dichlorophenylacetonitrile in 500 ml of tetrahydrofuran is added dropwise at 20° C., in the course of 30 minutes, then the reaction mixture is stirred at room temperature for 2 hours. The mixture is cooled to −20° C. and a solution of 98 g of 1-bromo-2-tetrahydropyranyloxyethane in 100 ml of tetrahydrofuran is added, the mixture is allowed to return to room temperature and after two hours a solution of 50 g of ammonium chloride in 3 liters of water is added. The mixture is extracted with 1.5 liters of ether, washed with a saturated sodium chloride solution, separated after settling has taken place, dried over $MgSO_4$ and concentrated in vacuo.

The residue is chromatographed on silica gel, eluent: dichloromethane. The pure product fractions are concentrated in vacuo to yield 83.6 g of an oil.

B) 1-Amino-2-(3,4-dichlorophenyl)-4-(2-tetrahydropyranyloxy)butane.

83.6 g of the nitrile obtained above are dissolved in 100 ml of absolute ethanol. 350 ml of concentrated ammonia are added and then, while flushing with nitrogen, Raney nickel is added (10% of the quantity of starting amine). The mixture is then hydrogenated under a hydrogen atmosphere at room temperature and atmospheric pressure.

11.9 liters of hydrogen are absorbed in 3 hours. The catalyst is separated by filtration on Celite, the filtrate is concentrated in vacuo, and the residue is taken up in a saturated sodium chloride solution. After extraction with ether and drying over $MgSO_4$, 82.5 g of an oil are obtained.

C) 1-Ethoxycarboxamido-2-(3,4-dichlorophenyl)-4-(2-tetrahydropyranyloxy)butane.

10.1 g of triethylamine, then 10.8 g of ethyl chloroformate, are added to 31.8 g of product obtained above dissolved in 150 ml of dichloromethane. The mixture is stirred for half an hour at room temperature, washed with water, dried over sodium sulphate and evaporated to dryness.

D) 1-Methylamino-2-(3,4-dichlorophenyl)-4-(2-tetrahydropyranyloxy)butane.

The oil obtained above dissolved in 150 ml of tetrahydrofuran is added to a suspension of 7.6 g of lithium aluminium hydride in 100 ml of tetrahydrofuran under reflux. After refluxing for two hours the mixture is cooled, 30 ml of 5N sodium hydroxide are added, the precipitate is filtered and the solution is evaporated.

E) 1-N-Methylbenzoylamino-2-(3,4-dichlorophenyl)-4-(2-tetrahydropyranyloxy)butane.

14.05 g of benzoyl chloride dissolved in 50 ml of dichloromethane are added dropwise to a solution of the product obtained above and 10.1 g of triethylamine in 150 ml of dichloromethane. The mixture is stirred for half an hour at room temperature and evaporated to dryness, and the residue is taken up in ether, washed with water, dried over sodium sulphate and evaporated to dryness. The residue is purified by silica gel chromatography, eluent: dichloromethane/ethyl acetate 9:1 (v/v).

28.5 g of a colourless oil are obtained.

F) 1-N-Methylbenzoylamino-2-(3,4-dichlorophenyl)-4-hydroxybutane.

15 ml of an ether solution saturated with hydrochloric acid are added to a solution of 21.7 g of product obtained above in 150 ml of methanol, the mixture is stirred for half an hour at room temperature and evaporated to dryness, and the product is crystallised in ether.

16.9 g are thus obtained.

M.p.=137°–139° C.

G) 1-N-Methylbenzoylamino-2-(3,4-dichlorophenyl)-4-mesyloxybutane.

4.6 g of methyl chloride dissolved in 25 ml of dichloromethane are added dropwise to 14 g of the product obtained above and 4 g of triethylamine dissolved in 100 ml of dichloromethane. The mixture is stirred for one hour at room temperature and evaporated to dryness, the residue is taken up in ethyl acetate and the mixture is washed with ether.

15.4 g are thus obtained.

M.p.=100°–102° C.

H) Compound 8

1 g of the product obtained above, is added to 2 g of 4-N-acetylanilinopiperidine, then the mixture is dissolved in 5 ml of dimethylformamide. The reaction mixture is heated at 80° C. for two hours and then ice is added, the mixture is extracted with ether, and the ethereal phase is washed with water, dried over $MgSO_4$ and concentrated in vacuo. The residue is chromatographed on silica gel, eluent: dichloromethane/methanol 98:2 (v/v).

Concentration of the pure fractions yields a residue which is taken up in dichloromethane and then ethereal hydrogen chloride is added and the hydrochloride is separated by filtration.

m=0.92 g

M.p.=108° C. (decomposition).

The compounds 9, 10 and 11 assembled in Table 2 are prepared by the procedures according to Examples 7 or 8 above.

TABLE 2

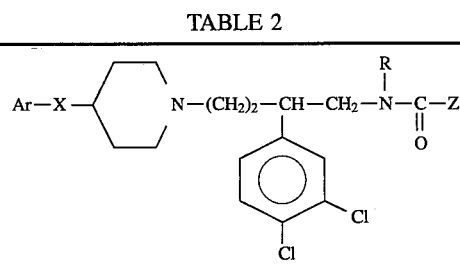

| Example n° | Z | Ar—X— | R | F;°C. | Salt |
|---|---|---|---|---|---|
| 9 | naphthyl-F | phenyl-NH— | H | 175 | 2HCl |
| 10 | phenyl-O-CH(CH₃)₂ | phenyl-NH— | —CH₃ | 205–207 | 2HCl |

TABLE 2-continued

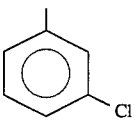

| Example n° | Z | Ar—X— | R | F;°C. | Salt |
|---|---|---|---|---|---|
| 11 | 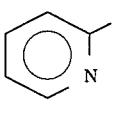 | 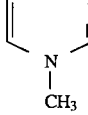 | —CH₃ | 105 | 2HCl |

EXAMPLE 12

N-[4-(4-(1-Methyl-2-imidazolyl)thio-1-piperidinyl)-2-naphthylbutyl]-2,4-dimethoxybenzamide dihydrochloride (compound 12)

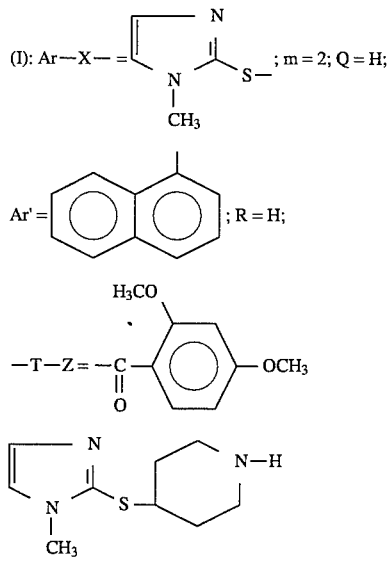

A)—Preparation of the amine

The amine above is prepared by the procedure according to Example 1A and by replacing the phenol by 1-methyl-2-mercaptoimidazole.

M.p.=209° C. (hydrochloride)

B) Compound 12

2.8 g of 1-(2,4-dimethoxybenzoylamino)-2-(1-naphthyl)-4-mesyloxybutane prepared by the procedure according to Example 1 are heated at 80° C. for one and a half hours in the presence of 1.35 g of the amine prepared above and of 2.02 g of triethylamine in 8 ml of dimethylformamide. The reaction mixture is then allowed to cool and thereafter ice-cold water is added. The precipitate obtained is separated by filtration and dissolved in dichloromethane. The solution is washed with water, then the organic phase is dried over MgSO₄ and concentrated in vacuo. The residue is chromatographed on silica gel, eluent: dichloromethane/methanol 100:2 (v/v).

Concentration of the pure products yields a residue which is taken up in dichloromethane and then ethereal hydrogen chloride is added. The hydrochloride is separated by filtration.

m=0.25 g

M.p.=146°–150° C.

The compounds described in Table 2 are prepared by the procedure according to Example 12.

TABLE 3

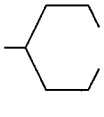

| Example n° | Z | F;°C. | Salt |
|---|---|---|---|
| 13 | 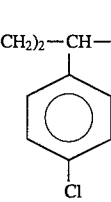 | 215 | 2HCl |
| 14 |  | 186 | 2HCl |

EXAMPLE 15

(−)-N-Methyl[4-(4-anilino-1-piperidinyl)-2-(3,4-dichlorophenyl)butyl]-4-fluoro-1-naphthalenecarboxamide dihydrochloride

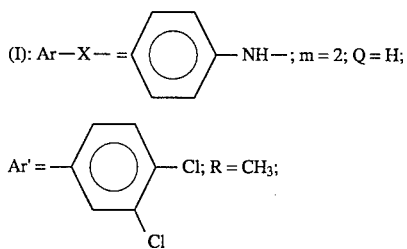

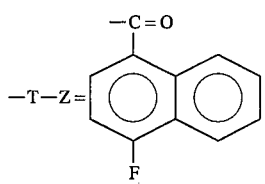

The (−) enantiomer of the compound above is prepared starting from the racemic amino alcohol, the enantiomers of which are separated according to the method described in Patent Application EP-A-428434, as indicated below.
(+)-1-Amino-2-(3,4-dichlorophenyl)-4-butanol enantiomer.

93 g of the racemic amino alcohol, dissolved in 300 ml of methanol, are added to 59.65 g of D-(−)-tartaric acid dissolved in 2 liters of methanol heated to reflux. The temperature is allowed to return to room temperature, and the crystals are filtered, washed with methanol and dried in vacuo at 50° C. over $P_2O_5$.

m=64.8 g
$[\alpha]_D^{20}$=−5.2° (c=1 in water)

The product is then recrystallised in 2.96 l of methanol, and the crystals are filtered, washed with methanol and dried in vacuo at 50° C. over $P_2O_5$.

m=45.3g
$[\alpha]_D^{20}$=−4.5° (c=1 in water)
M.p.=201° C.

The D-(−)-tartrate is taken up in 250 ml of water the mixture is rendered alkaline with a concentrated sodium hydroxide solution and extracted 3 times with 200 ml of dichloromethane, washed with a saturated sodium chloride solution and separated after settling has taken place, and the organic phase was dried over $MgSO_4$, filtered and concentrated in vacuo. The residue is taken up in isopropyl ether, the mixture is stirred for one hour at room temperature, and the crystals are filtered and washed with isopropyl ether.

m=24.7g
$[\alpha]_D^{20}$=+9.0° (c=1 in methanol)
M.p.=79°−80° C.

-1-Amino-2-(3,4-dichlorophenyl)-4-butanol enantiomer.

Proceeding as above and using L-(+)-tartaric acid the (−) enantiomer is obtained.
$[\alpha]_D^{20}$=−9.2° (c=1 in methanol)
M.p.=79°−80° C.

A) 1-Amino-2-(3,4-dichlorophenyl)-4-(2-tetrahydropyranyloxy)butane.

12.50 g of (+)-1-amino-2-(3,4-dichlorophenyl)-4-butanol are dissolved in a mixture of 150 ml of dichloromethane and 50 ml of DMF. Ether saturated with hydrochloric acid is added to pH=12, then 5.39 g of tetrahydropyran are added and the reaction mixture is heated to reflux for one hour. The solvents are concentrated in vacuo, the residue is taken up in ether and the precipitate is separated by filtration.

m=15.5 g.

B) 2-(3,4-Dichlorophenyl)-4-(2-tetrahydropyranyloxy)-4-fluoro-1-naphthalenecarboxamide.

15.5 g of the product prepared above are dissolved in 100 ml of dichloromethane in the presence of 13.3 g of triethylamine. 10.6 g of 4-fluoronaphthoyl chloride dissolved in 10 ml of dichloromethane are added and the reaction mixture is then left for 3 hours at room temperature with stirring. The solvents are concentrated in vacuo, the residue is taken up in water, and the mixture is extracted with ethyl acetate and washed successively with a 10% NaOH solution, with water and then with a saturated NaCl solution. The organic phases are dried over $MgSO_4$ and concentrated in vacuo.

m=21 g.

C) N-Methyl[2-(3,4-dichlorophenyl)-4-(2-tetrahydropyranyloxy)butane]-4-fluoro-1-naphthalenecarboxamide.

1.56 g of 55% NaH are suspended in 60 ml of DMF and 21.3 g of the product prepared above dissolved in 120 ml of DMF are then added slowly. The mixture is stirred for 15 minutes and then 12.3 g of methyl iodide dissolved in 20 ml of DMF are added dropwise. The reaction mixture is stirred at room temperature for half an hour and then concentrated in vacuo. The residue is taken up in water, and the water is then washed with a saturated NaCl solution. The ethereal phase is dried over taken up in water, extracted with ether, washed with water and then with a saturated NaCl solution. The ethereal phase is dried over $MgSO_4$ and then concentrated in vacuo.

m=18.6 g.

D) N-Methyl[2-(3,4-dichlorophenyl)-4-butanol]-4-fluoro-1-naphthalenecarboxamide.

18.57 g of the product prepared above are dissolved in 300 ml of methanol and 2 ml of ether saturated with hydrochloric acid are then added and the reaction mixture is then heated to reflux for 5 hours. The solvents are concentrated in vacuo, the residue is taken up in a 2N HCl solution, the mixture is extracted with ether and the extract is washed successively with water, a 5% $NaHCO_3$ solution, with water and then with a saturated NaCl solution. The etheral phase is concentrated in vacuo and the residue is chromatographed on silica gel, eluent: $CH_2Cl_2/CH_3OH$ 97:3 (v/v). The fractions of pure product are concentrated in vacuo.

m=9.31 g
$[\alpha]_D^{20}$=−31.8° (c=1 in methanol)
M.p.=125°−127° C.

EXAMPLE 16

(−)-4-(α-Methylanilino)-N(a)-methyl [2-(3,4-dichlorophenyl) -4-(4-fluoro-1-naphthalenecarboxamino)-N'-methylbutyl]piperidinium iodide

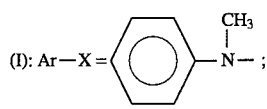

$Q' = CH_3$; $A^\ominus = I^\ominus$; $Q = H$;

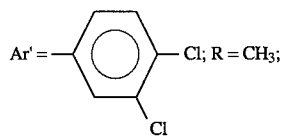

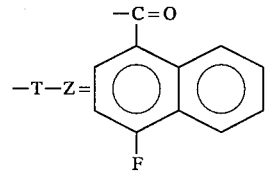

2.41 g of the compound prepared above according to Example 15, in the form of free base, 24 ml of methyl iodide and 1 ml of acetone are left with stirring at room temperature for 24 hours.

The reaction mixture is concentrated in vacuo and the residue is chromatographed on silica gel, eluent: $CH_2Cl_2/CH_3OH$ 97:3 (v/v).

The product eluted first corresponds to that in which the methyl on the nitrogen of the piperidine is in the axial position. Concentration of the corresponding fraction yields a residue which precipitates in ether.

m=1.11 g
M.p.=152°–154° C.
$[\alpha]_D^{20}=-28.3°$ (c=1 in methanol)

EXAMPLE 17

4-(α-Methylanilino)-N(a)-methyl [2-(3,4-dichlorophenyl) -4-(3-isopropoxyphenylbenzamido)- N'-methylbutyl]piperidinium iodide

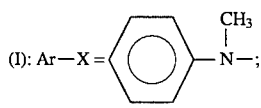

Q' = CH$_3$; A$^\ominus$ = I$^\ominus$; Q = H;

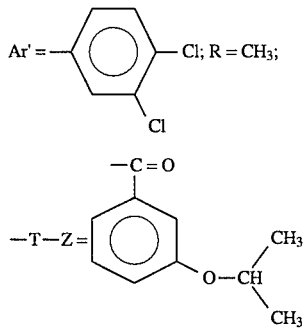

Proceeding according to Example 16, but starting from the compound described in Example 10, in the form of free base, the compound above is prepared.

M.p.=131°–133° C.
$^{13}$C NMR spectrum:

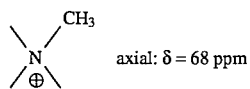

We claim:
1. A process for the preparation of compounds having the formula:

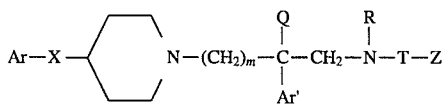

in which:
m is equal to 2 or 3;

Ar represents a phenyl, unsubstituted or substituted one or more times with a halogen atom, with a C$_1$–C$_3$ alkyl, with a trifluoromethyl, with an alkoxy in which the alkyl is a C$_1$–C$_3$ group, with a hydroxyl or with a methylenedioxy; a thienyl, pyridyl or imidazolyl group which is or is not substituted with a C$_1$–C$_3$ alkyl;

Ar' represents a phenyl group, unsubstituted or mono- or di-substituted with a halogen atom, with a C$_1$–C$_3$ alkyl, with a trifluoromethyl, with an alkoxy in which the alkyl is a C$_1$–C$_3$ group, with a hydroxyl or with a methylenedioxy; a thienyl group; an imidazolyl group or a benzothienyl group, each of which is unsubstituted or substituted with a halogen; a naphthyl group unsubstituted or substituted with a halogen; a biphenyl group; an indolyl unsubstituted or substituted on the nitrogen with a benzyl group;

X represents an oxygen atom, a sulphur atom, a sulphone or a sulphoxide, an

group, an

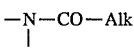

group or an

group in which Alk is a C$_1$–C$_3$ alkyl group; an

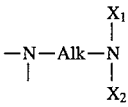

group in which Alk represents a C$_1$–C$_3$ alkylene and X$_1$ and X$_2$ represent, independently, hydrogen, a C$_1$–C$_3$ alkyl or form, together with the nitrogen atom to which they are bonded, a pyrrolidine or a piperidine heterocycle;

Q represents hydrogen, a C$_1$–C$_4$ alkyl group or an aminoalkyl group of formula —(CH$_2$)$_q$—Am', where q is 2 or 3 and Am' is a piperidino, 4-benzylpiperidino or di(C$_1$–C$_4$)alkylamino group;

R represents hydrogen, a methyl group or a group (CH$_2$)$_n$—L, where n is an integer from 2 to 6 and L is hydrogen or an amino group;

T represents a group selected from

W being an oxygen or sulphur atom, and
Z represents either M or OM when T represents the

group, or M when T represents the group

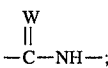

M represents hydrogen or a linear or branched C$_1$–C$_6$ alkyl; an α-hydroxybenzyl, an α-alkylbenzyl or a phenylalkyl in which the alkyl contains 1 to 3 carbon atoms, in which the phenyl portion is unsubstituted, mono- or polysubstituted on the aromatic ring with a halogen, a hydroxyl, an alkoxy of 1 to 4 carbon atoms, an alkyl of 1 to 4 carbon atoms; a pyridylalkyl in which the alkyl group contains 1 to 3 carbon atoms; a naphthylalkyl in which the alkyl group contains 1 to 3 carbon atoms; a pyridylthioalkyl in which the alkyl group contains 1 to 3 carbon atoms; a styryl; a 1-methyl-2-imidazolylthioalkyl in which the alkyl group contains 1 to 3 carbon atoms; a 1-oxophenyl-3-indan-2-yl; an aromatic or heteroaromatic radical selected from the group consisting of a phenyl which is unsubstituted, mono-or polysubstituted by a halogen, a $C_1$–$C_4$ alkyl, a $C_1$–$C_4$ alkoxy or a hydroxyl; a naphthyl group which is unsubstituted, mono- or polysubstituted by a halogen, a $C_1$–$C_4$ alkyl or a hydroxyl; a pyridyl, a thienyl, an indolyl and a benzothienyl, said pyridyl, thienyl, indolyl and benzothienyl groups being unsubstituted, mono- or polysubstituted by a $C_1$–$C_4$ alkyl or hydroxyl;

or a salt thereof with an inorganic or organic acid or a quaternary ammonium salt thereof, comprising:

a) treating a free amine of formula:

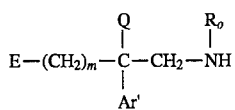  (II)

in which m, Ar', and Q are defined above;

R° represents hydrogen, a methyl group or a group $(CH_2)_n$—L°, where n is an integer from 2 to 6 and L° is hydrogen or an amino group protected by an N-protecting group hydrolysable in an acidic medium; and E represents a tetrahydro-2-pyranyloxy group or a group

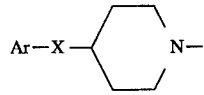

where Ar and X are defined above;

either with a functional derivative of an acid of formula:

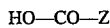  (III)

in which Z is defined above, when a compound of formula (I) in which T is a —CO— is to be prepared, or with an iso(thio) cyanate of formula:

  (III')

in which W and Z are defined above;

when a compound of formula (I) in which T is —C(W)—NH— is to be prepared, to form the compound of formula:

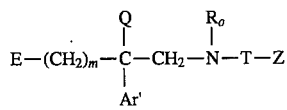  (IV)

b) removing from the compound of formula (IV) the tetrahydropyranyl group by acid hydrolysis, it alternatively being possible for the hydrolysis to take place in step (a) on the starting amine of formula (II), c) treating the N-substituted alkanolamine thereby obtained of formula

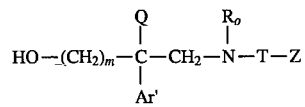  (V)

with methanesulphonyl chloride, d) reacting the mesylate thereby obtained of formula:

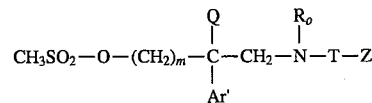  (VI)

with a secondary amine of formula:

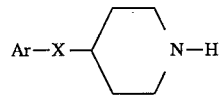  (VII)

in which Ar and X are defined above, e) removing the N-protecting groups, where appropriate, and optionally converting the product thereby obtained to one of its salts.

2. A stereoselective process for the preparation of optically pure compounds having the formula:

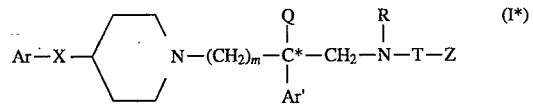  (I*)

in which:

"*" denotes that the carbon atom thus marked has determined a (+) or (−) absolute configuration;

m is equal to 2 or 3;

Ar represents a phenyl, unsubstituted or substituted one or more times with a halogen atom, with a $C_1$–$C_3$ alkyl, with a trifluoromethyl, with an alkoxy in which the alkyl is a $C_1$–$C_3$ group, with a hydroxyl or with a methylenedioxy; a thienyl, pyridyl or imidazolyl group which is or is not substituted with a $C_1$–$C_3$ alkyl;

Ar' represents a phenyl group, unsubstituted or mono- or di-substituted with a halogen atom, with a $C_1$–$C_3$ alkyl, with a trifluoromethyl, with an alkoxy in which the alkyl is a $C_1$–$C_3$ group, with a hydroxyl or with a methylenedioxy; a thienyl group; an imidazolyl group or a benzothienyl group, each of which is unsubstituted or substituted with a halogen; a naphthyl group unsubstituted or substituted with a halogen; a biphenyl group; an indolyl unsubstituted or substituted on the nitrogen with a benzyl group;

X represents an oxygen atom, a sulphur atom, a sulphone or a sulphoxide, an

group, an

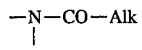

group or an $$-\underset{|}{N}-Alk$$

group in which Alk is a $C_1$–$C_3$ alkyl group; an $$-\underset{|}{N}-Alk-\underset{|}{\overset{X_1}{N}}\\ \phantom{-N-Alk-N}X_2$$

group in which Alk represents a $C_1$–$C_3$ alkylene and $X_1$ and $X_2$ represent, independently, hydrogen, a $C_1$–$C_3$ alkyl or form, together with the nitrogen atom to which they are bonded, a pyrrolidine or a piperidine heterocycle;

Q represents hydrogen, a $C_1$–$C_4$ alkyl group or an aminoalkyl group of formula —$(CH_2)_q$—Am', where q is 2 or 3 and Am' is a piperidino, 4-benzylpiperidino or di($C_1$–$C_4$)alkylamino group;

R represents hydrogen, a methyl group or a group $(CH_2)_n$—L, where n is an integer from 2 to 6 and L is hydrogen or an amino group;

T represents a group selected from $$\underset{\phantom{x}}{\overset{O}{\underset{\|}{-C-}}} \quad \text{and} \quad \underset{\phantom{x}}{\overset{W}{\underset{\|}{-C-NH-}}}$$

W being an oxygen or sulphur atom, and

Z represents either M or OM when T represents the $$\overset{O}{\underset{\|}{-C-}}$$

group, or M when T represents the group $$\overset{W}{\underset{\|}{-C-NH-}};$$

M represents hydrogen or a linear or branched $C_1$–$C_6$ alkyl; an α-hydroxybenzyl, an α-alkylbenzyl or a phenylalkyl in which the alkyl contains 1 to 3 carbon atoms, in which the phenyl portion is unsubstituted, mono- or polysubstituted on the aromatic ring with a halogen, a hydroxyl, an alkoxy of 1 to 4 carbon atoms, and alkyl of 1 to 4 carbon atoms; a pyridylalkyl in which the alkyl group contains 1 to 3 carbon atoms; a naphthylalkyl in which the alkyl group contains 1 to 3 carbon atoms; a pyridylthioalkyl in which the alkyl group contains 1 to 3 carbon atoms; a styryl; a 1-methyl-2-imidazolylthioalkyl in which the alkyl group contains 1 to 3 carbon atoms; a 1-oxophenyl-3-indan-2-yl; an aromatic or heteroaromatic radical selected from the group consisting of a phenyl which is unsubstituted, mono-or polysubstituted by a halogen, a $C_1$–$C_4$ alkyl, a $C_1$–$C_4$ alkoxy or a hydroxyl; a naphthyl group which is unsubstituted, mono- or polysubstituted by a halogen, a $C_1$–$C_4$ alkyl or a hydroxyl; a pyridyl, a thienyl, an indolyl and a benzothienyl, said pyridyl, thienyl, indolyl and benzothienyl groups being unsubstituted, mono- or polysubstituted by a $C_1$–$C_4$ alkyl or hydroxyl;

or a salt thereof with an inorganic or organic acid or a quaternary ammonium salt thereof, comprising:

(a) treating a compound of formula:

$$\underset{\text{Ph}}{\bigcirc}-\underset{\underset{CH_3}{|}}{\overset{H}{\underset{|}{C^*}}}-\underset{\phantom{x}}{\overset{H}{\underset{|}{N}}}-\underset{\phantom{x}}{\overset{\phantom{x}}{\underset{\|}{C}}}{\underset{O}{\|}}(CH_2)_{m-1}-\underset{\underset{Ar'}{|}}{\overset{Q}{\underset{|}{C}}}-CH_2-NHR^o \qquad (XVII^*)$$

in a solvent, in acidic medium, to yield an amino acid of formula:

$$HO-\underset{\underset{O}{\|}}{\overset{\phantom{x}}{\underset{\|}{C}}}-(CH_2)_{m-1}-\underset{\underset{Ar'}{|}}{\overset{Q}{\underset{|}{C^*}}}-CH_2-NHR^o \qquad (XVIII^*)$$

(b) esterifying the amino acid of formula (XVIII*) in an alcohol AlkOH, where Alk is an alkyl of 1 to 4 carbon atoms, in acidic medium, (c) treating the corresponding ester of formula:

$$AlkO-\underset{\underset{O}{\|}}{\overset{\phantom{x}}{\underset{\|}{C}}}-(CH_2)_{m-1}-\underset{\underset{Ar'}{|}}{\overset{Q}{\underset{|}{C^*}}}-CH_2-NHR^o \qquad (XIX^*)$$

in which Alk is an alkyl of 1 to 4 carbon atoms, and in which m, Q, and Ar' are defined above, and wherein R° represents hydrogen, a methyl group or a group $(CH_2)_n$—L°, where n is an integer from 2 to 6 and L° is hydrogen or an amino group protected by an N-protecting group hydrolysable in an acidic medium, either with a functional derivative of an acid of formula:

$$HO-C-Z \qquad (III)$$

or with an iso(thio)cynate of formula:

$$W=C=N-Z \qquad (III')$$

in which W and Z are defined above;

(d) subjecting the ester thus obtained of the formula:

$$AlkO-\underset{\underset{O}{\|}}{\overset{\phantom{x}}{\underset{\|}{C}}}-(CH_2)_{m-1}-\underset{\underset{Ar'}{|}}{\overset{Q}{\underset{|}{C^*}}}-CH_2-\underset{\phantom{x}}{\overset{R^o}{\underset{|}{N}}}-T-Z \qquad (XX^*)$$

to the action of a reducing agent; and (e) converting the corresponding alcohol of formula:

$$HO-(CH_2)_m-\underset{\underset{Ar'}{|}}{\overset{Q}{\underset{|}{C^*}}}-CH_2-\underset{\phantom{x}}{\overset{R_o}{\underset{|}{N}}}-T-Z \qquad (V^*)$$

into its methanesulphonate ester of formula:

$$CH_3SO_2-O-(CH_2)_m-\underset{\underset{Ar'}{|}}{\overset{Q}{\underset{|}{C^*}}}-CH_2-\underset{\phantom{x}}{\overset{R_o}{\underset{|}{N}}}-T-Z \qquad (VI^*)$$

and;

(f) treating said methanesulphonate ester of formula (VI*) with an amine of formula:

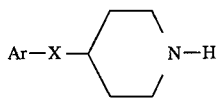 (VII)

in which Ar and X are defined above,
to produce a compound of formula (I*).

3. The process as claimed in claim 1, wherein Ar' is selected from the group consisting of a phenyl group which is mono- or disubstituted with a chlorine or fluorine atom, a thienyl, imidazolyl or benzothienyl group which is substituted with a chlorine or fluorine atom, and a napththyl group which is substituted with a fluorine.

4. The process as claimed in claim 2, wherein Ar represents a phenyl group which is mono-or disubstituted with a chlorine or fluorine atom.

5. The process as claimed in claim 2, wherein Ar' is selected from the group consisting of a phenyl group which is mono- or disubstituted with a chlorine or fluorine atom, a thienyl, imidazolyl or benzothienyl group which is substituted with a chlorine or fluorine atom, and a napththyl group which is substituted with a fluorine.

6. A process according to claim 13, wherein Ar represents a phenyl substituted with a chlorine atom.

7. A process to claim 1, wherein Ar represents a phenyl substituted with a fluorine atom.

* * * * *